United States Patent [19]

Kulle

[11] 4,095,810
[45] Jun. 20, 1978

[54] GILL-TYPE TIP PROTECTOR FOR SEALING OPEN TUBES AND THE LIKE

[75] Inventor: Lee K. Kulle, Mundelein, Ill.

[73] Assignee: Baxter Travenol Laboratories, Inc., Deerfield, Ill.

[21] Appl. No.: 760,208

[22] Filed: Jan. 17, 1977

[51] Int. Cl.² .............................................. F16J 15/10
[52] U.S. Cl. ..................................................... 277/208
[58] Field of Search ............... 138/96, 89; 277/207 R, 277/208

[56] References Cited

U.S. PATENT DOCUMENTS

| 1,287,285 | 12/1918 | Gammeter | 277/208 |
| 3,325,175 | 6/1967 | Lower | 277/208 |
| 3,847,183 | 11/1974 | Meyer | 138/96 R |

Primary Examiner—Robert I. Smith
Attorney, Agent, or Firm—Paul C. Flattery; John P. Kirby, Jr.; Gary W. McFarron

[57] ABSTRACT

A tubular sealing member defines a bore having an open mouth, plus several spaced, annular sealing members in the bore to grip and seal a tubular projection. In accordance with this invention, at least some of the spaced, annular sealing rings define, in cross section, flexible elongated projections which, in turn, define longitudinal axes which incline toward the open mouth in acute angle relationship to the axis of the bore. The longitudinal axes of the projections are at least 0.01 inch long. The average thickness of each of the flexible projections is less than the length of its longitudinal axis.

4 Claims, 4 Drawing Figures

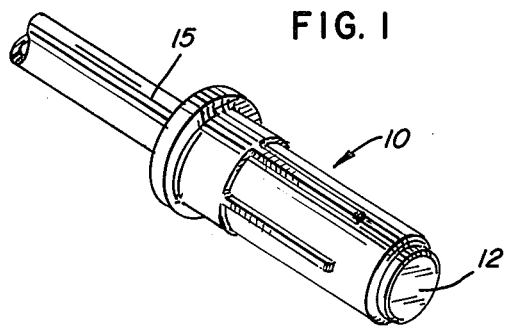
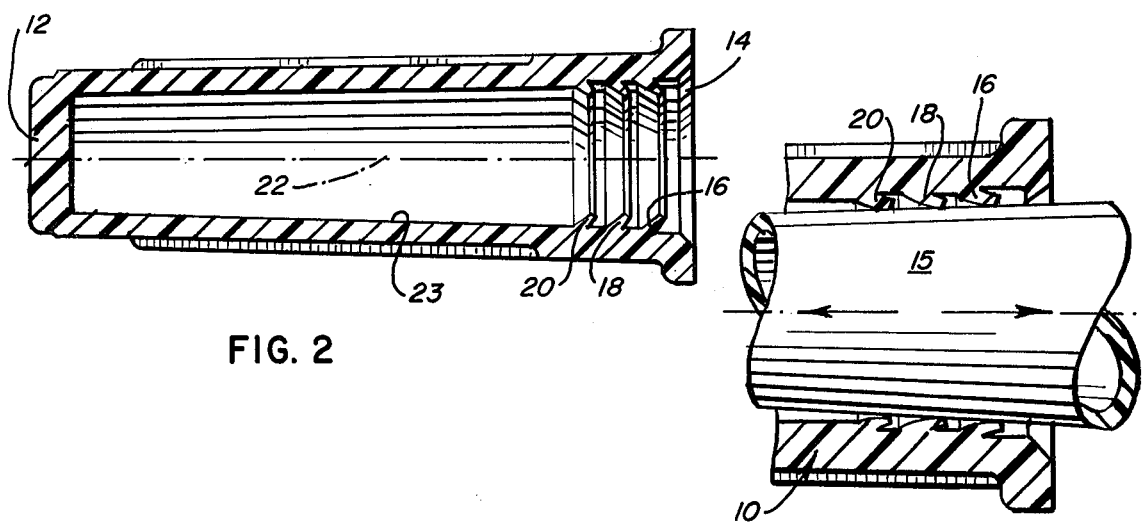
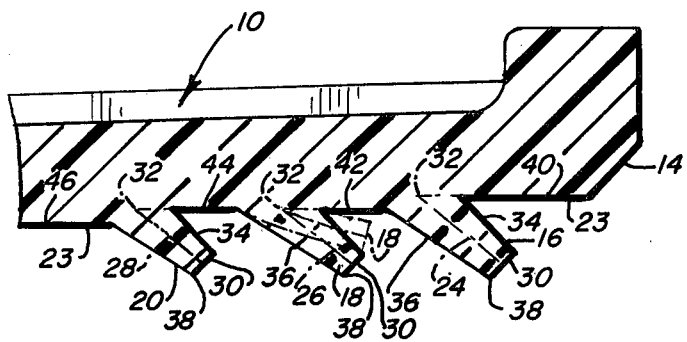

GILL-TYPE TIP PROTECTOR FOR SEALING OPEN TUBES AND THE LIKE

BACKGROUND OF THE INVENTION

In parenteral solution administration sets and many other types of medical equipment tubular hubs, needle-receiving luers, and the like are utilized which must be sealed in a sterile manner until ready for opening and use.

Accordingly, a semi-rigid tube is provided to fit over the hub or luer as a removable sealing closure, the semi-rigid tube having a bore which may define several spaced annular sealing members. These are generally semi-cylindrical in shape, extending in circumferential manner about the axis of the bore. The annular sealing members are proportioned to press against a rigid, cylindrical surface of the tube to be sealed, providing several annular seal lines when in place, and yet permitting removal by simply twisting and pulling of the rigid sealing tube.

Such an arrangement, however, has the disadvantage that it exhibits a very sensitive tolerance of only one or two thousandths of an inch. In other words, if the sealing caps happen to be made with an inner diameter which is off of specification by more than two or three thousandths of an inch, the caps may either not fit on the desired luer or other tube to be sealed, or they will fit so loosely that they will fail to perform the desired sealing function. Similarly, if the outer diameter of the luer to be sealed is out of specification for any reason by two or three thousandths of an inch, the same effect may happen.

The above also indicates that separately-designed and molded sealing caps must be provided for each type of luer or other tube to be sealed, even if the variation in outer diameter between the various types is only two or three thousandths of an inch.

Furthermore, tip protectors which utilize, in their inner diameter, semi-cylindrical, annular sealing rings may be very difficult to mold. It has been found experimentally that, referring to medical-type tip protectors exhibiting an inner diameter of about 0.27 inch, it has been exceedingly difficult to mold semi-cylindrical, annular sealing rings which are as much as 0.01 inch in radius, in that such large sealing rings tend to rip as they are being removed from the mold. The only way to accomplish this would be to substantially increase the draft angle of the mold, or to use a much softer plastic molding material than is customarily used in this type of operation.

An example of a tip protector using such semi-cylindrical annular sealing rings is shown in U.S. Pat. No. 3,889,673. Other annular sealing structures are shown in U.S. Pat. Nos. 3,101,841; 2,752,059; and 3,583,591.

In accordance with this invention, a tip protector is provided which is capable of being used to seal tubular parts which may have a substantial size variation. In the specific embodiment shown, the tip protector of this invention is capable of sealing tubular parts which vary in outer diameter by up to about nine percent. Accordingly, quality control problems in the manufacture of sealed parenteral solution administration sets and similar medical items is greatly simplified, and a single design of tip protector can be used with varying designs of tubular members to be sealed.

Furthermore, the annular sealing members utilized in this invention may have a length which is substantially greater than 0.01 inch, while being readily moldable without damaging of the annular sealing rings on removal from the mold, even when a normal draft angle or taper is used on the mold (for example two degrees), and when normally stiff plastic formulations such as low density polyethylene are used for molding the tip protectors of this invention.

DESCRIPTION OF THE INVENTION

In accordance with this invention, a tubular sealing member defining a bore and an open mouth is provided, further defining a plurality of spaced, annular sealing members in the bore, to grip a tube to be sealed. In this invention, a plurality of the spaced, annular sealing rings define, in cross section, flexible, elongated projections which, in turn, define longitudinal axes which incline toward the open mouth in acute angle relationship to the axis of the bore. The longitudinal axes of the projections are at least 0.01 inch long, with the average thickness of each of such projections being less than the length of its longitudinal axis.

As a result of this, the sealing rings define angularly-related, elongated "gills", rather than the typical semi-cylindrical, annular projections. Because of this, the gill-type sealing rings may be flexible, and bend outwardly when surrounding and gripping a tube to be sealed. Because of this capability to bend outwardly, a significant variation in the relative size of the tube to be sealed is possible without disruption of the sealing capability of the sealing member of this invention.

Furthermore, the structure of this invention can be removed from its mold with a substantially reduced risk of tearing of the sealing rings, despite their increased length over that of the prior art, because of their flexibility.

Preferably, the cross sectional projections of the sealing rings taper to a minimum width at their outer ends, and their outer ends preferably define generally flat, annular inner surfaces defining an acute angle with the axis of the bore of the tubular sealing member. This provides an annular, innermost edge on the sealing rings which can bear against the tube to be sealed with focused sealing pressure, for improved sealing characteristics.

The lengths of the longitudinal axes of the cross sectional projections of the sealing rings are preferred to consecutively decrease from the outermost ring, nearest the open mouth, to the innermost sealing ring. However, the annular sealing edges of the separate sealing rings are generally equidistant from the axis of the bore, to provide equal sealing opportunity for each ring.

It is also preferred for the inner diameter of the bore between the open mouth and the first sealing ring nearest the open mouth to be greater than the inner diameter of the bore between the nearest sealing ring and the next sealing ring adjacent thereto. Similarly, the inner diameter of the bore between consecutive sealing rings may, if desired, continue to decrease in the direction inwardly of the sealing member from the open mouth. This facilitates the folding of the sealing rings flush with the surface of the bore, which is advantageous upon removing of the sealing member of its mold, and also when receiving a relatively large tube to be sealed.

Referring to the drawings,

FIG. 1 is a perspective view of the sealing member of this invention, shown closing and sealing a luer of a parenteral solution administration set.

FIG. 2 is a longitudinal sectional view of the tubular sealing member of this invention.

FIG. 3 is a longitudinal sectional view of the sealing member of this invention shown in sealing relation with respect to a luer as in FIG. 1.

FIG. 4 is a greatly enlarged, fragmentary, longitudinal sectional view of a portion of the sealing member of this invention.

Referring to the drawings, tubular sealing member 10 is shown made out of a semi-flexible, plastic material such as low-density polyethylene or the like. Tubular sealing member 10 defines an integral, closed end 12, although, alternatively, end 12 may be open and sealed if desired with a wad of cotton or an air-permeable filtering membrane, if such is desired.

Sealing member 10 defines at its other end an open mouth 14 for receiving a luer 15 or the like to be sealed.

Spaced from open mouth 14 are a plurality of spaced, annular sealing rings 16, 18, 20 which project from the bore of tubular member 10, and extend completely around the axis 22 of the bore in circumferential manner. The cross-sectional projections of rings 16, 18, 20, in turn, define longitudinal axes 24, 26, 28 which incline toward open mouth 14 in acute angle relationship to the axis 22 of the bore of sealing member 10.

The lengths of longitudinal axes 24, 26, 28 may be defined as extending from the inner ends 30 of rings 24, 26, 28, to the intersections 32 of the cylindrical planes 40, 42, 44 of the bore-defining wall 23 and the ends of the respective axes 24, 26, 28, as shown in FIG. 4.

The longitudinal axes 24, 26, 28 of each of the cross sectional projections of rings 16, 18, 20 are at least 0.01 inch long, to facilitate the outward flexing of the sealing rings as shown in FIG. 3. Preferably, axis 24 may be about 0.043 inch long; axis 26 may be about 0.035 inch long; and axis 28 may be about 0.030 inch long, the lengths of the axes diminishing from axis 24 to axis 28.

The thicknesses of the cross sectional projections of rings 16, 18, 20 preferably taper to a minimum thickness at their inner ends 30, as shown in FIG. 4. This minimum thickness may preferably be about 0.01 to 0.15 inch, for example, 0.011 inch. The respective inner and outer sides 34, 36 of the rings can diverge outwardly at an angle of, for example, 15°, to provide an increasing thickness as one proceeds from the free inner end 30 to the outer end, which is integral with the rest of sealing member 10.

Sealing rings 16, 18, 20 define flat, annular inner surfaces (or cross-sectional projection ends) 30, positioned in acute angular relationship to axis 22 of the bore, to define an annular, innermost angled edge 38 which, as shown in FIG. 4, engages the tube to be sealed, providing a series of focused, annular sealed areas of relatively reduced area and relatively high sealing pressure. Also as shown in FIG. 4, rings 16, 18, 20 fold outwardly, and are spaced apart a distance sufficient to permit the unhindered folding of the rings to a position flush with the bore-defining wall 23, when that is required for removal from the mold and for accomodation of a relatively thick tube to be sealed.

The angle of axes 24, 26 28 is preferably essentially from 30° to 60° to the axis 22 of the bore of sealing member 10. As specifically shown, the angle is essentially 45°.

It is also preferred for the inner diameter of the bore at area 40 between open mouth 14 and the sealing ring 16 which is nearest to the open mouth, to be greater than the inner diameter of the bore at area 42 between the nearest sealing ring 16 and the next sealing ring 18 adjacent thereto. Similarly, the inner diameter of the bore between all consecutive sealing rings may decrease in the direction inwardly of the sealing member from the open mouth. Specifically, the inner diameter of the bore at area 40 may be about 0.27 inch; at area 42 the inner diameter may be about 0.262 inch; at area 44 the inner diameter may be 0.252 inch; and at area 46 the inner diameter may be 0.238 inch. Alternatively, the inner diameter may not necessarily decrease from between the first and second sealing rings and the second and third rings, and subsequent rings if they are utilized.

Accordingly, the resulting structure provides a tip protector which is capable of sealing the tube to be sealed with a substantial tolerance of relative diameters, the tolerance depending, of course, upon the size of the tip protector and its specific construction. Also, the structures of this invention provide easier molding characteristics for the elongated, annular sealing rings utilized herein.

The above has been offered for illustrative purposes only, and is not for the purpose of limiting the invention of this application, which is as defined in the claims below.

That which is claimed is:

1. A tubular sealing member defining a bore and an open mouth, and further defining a plurality of spaced, annular sealing members in said bore to grip a tube to be sealed, the improvement comprising:

a plurality of said spaced, annular sealing rings defining, in cross section, flexible, elongated projections which, in turn, define longitudinal axes which incline toward said open mouth in acute angle relationship to the axis of said bore, the longitudinal axes of said projections being at least 0.01 inch long, the average thickness of each said projection being less than the length of its longitudinal axis, the inner diameter of said bore between the open mouth and the sealing ring nearest to said open mouth being greater than the inner diameter of said bore between consecutively inwardly positioned sealing rings and the inner diameter of the bore between consecutive sealing rings decreasing in value in the direction inwardly of said sealing member from said open mouth.

2. The tubular sealing member of claim 1, in which the lengths of the longitudinal axes of the cross sectional projections consecutively decrease from the outermost to the innermost sealing ring.

3. The tubular sealing member of claim 2 in which said sealing rings define generally flat, annular inner surfaces defining an acute angle to the axis of said bore.

4. The tubular sealing member of claim 2 in which the acute angle of said longitudinal axis of said projections with the axis of said bore is essentially from 30° to 60°.

* * * * *